United States Patent

Dugger, III

[11] Patent Number: 5,869,082
[45] Date of Patent: Feb. 9, 1999

[54] BUCCAL, NON-POLAR SPRAY FOR NITROGLYCERIN

[75] Inventor: Harry A. Dugger, III, Flemington, N.J.

[73] Assignee: Flemington Pharmaceutical Corp., Flemington, N.J.

[21] Appl. No.: 630,064

[22] Filed: Apr. 12, 1996

[51] Int. Cl.⁶ .............................. A61F 13/02; A61L 9/04
[52] U.S. Cl. ........................ 424/435; 424/434; 424/45
[58] Field of Search ................... 424/434, 435, 424/45

[56] References Cited

U.S. PATENT DOCUMENTS 5,428,006 6/1995 Bechgaard et al. .................. 514/3

FOREIGN PATENT DOCUMENTS

| 0448961 | 10/1991 | European Pat. Off. . |
| 2735M74 | 8/1964 | France . |
| 3246081 | 6/1984 | Germany . |
| 4038203 | 6/1992 | Germany . |

*Primary Examiner*—Carlos A. Azpuru
*Attorney, Agent, or Firm*—Omri M. Behr, Esq.

[57] ABSTRACT

A buccal aerosol spray using a non-polar solvent has now been developed which provides nitroglycerin for rapid absorption through the oral mucosa, resulting in fast onset of effect. The buccal aerosol spray of the invention comprises: propellant 50–95%, non-polar solvent 5–50%, nitroglycerin 0.001–15%, flavoring agent 0.05–5%.

16 Claims, 1 Drawing Sheet

$K(a) = K(m) + K(b) + K(u)$

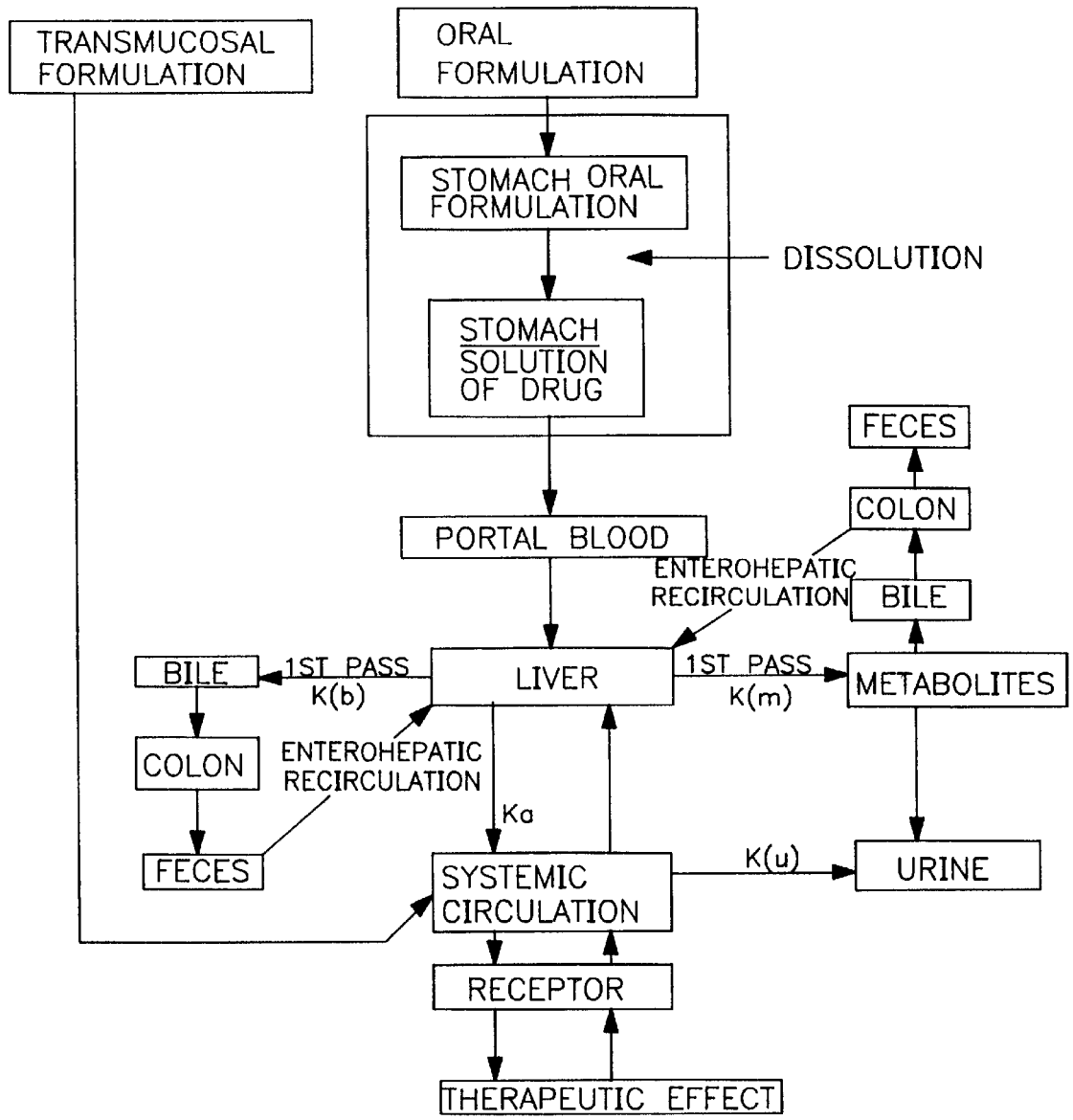

BUCCAL, NON-POLAR SPRAY FOR NITROGLYCERIN

BACKGROUND OF THE INVENTION

It is known that certain biologically active compounds are better absorbed through the oral mucosa than through other routes of administration, such as through the stomach or intestine. However, formulations suitable for such administration by these latter routes present their own problems. For example, the biologically active compound must be compatible with the other components of the composition such as propellants, solvents, etc. Many such formulations have been proposed. Klokkers-Bethke, describe a nitroglycerin spray for administration to the oral mucosa comprising nitroglycerin, ethanol, and other components. An orally administered pump spray is described by Cholcha in U.S. Pat. No. 5,186,925. Aerosol compositions containing a hydro-carbon propellant and a drug for administration to a mucosal surface are described in U.K. 2,082,457, Su, U.S. Pat. No. 3,155,574, Silson et al., U.S. Pat. No. 5,011,678, Wang et al., and by Parnell in U.S. Pat. No. 5,128,132. It should be noted that these references discuss bioavailability of solutions by inhalation rather than through the membranes to which they are admiministered.

SUMMARY OF THE INVENTION

A buccal aerosol spray using a non-polar solvent has now been developed which provides nitroglycerin for rapid absorption through the oral mucosa, resulting in fast onset of effect.

The buccal aerosol spray compositions of the present invention, for transmucosal administration of nitroglycerin soluble in a pharmacologically acceptable non-polar solvent are disclosed comprising in weight % of total composition: pharmaceutically acceptable propellant 50–95%, non-polar solvent 5–50%, nitroglycerin 0.1–6.5%, suitably additionally comprising, by weight of total composition a flavoring agent 0.05–5%. Preferably the composition comprises: propellant 55–85%, non-polar solvent 15–45%, nitroglycerin 0.2–3%, flavoring agent 0.1–2.5%; most suitably propellant 60–80%, non-polar solvent 19–32%, nitroglycerin 0.3–1.5 %, flavoring agent 1–2%.

It is an object of the invention to coat the mucosal membranes with extremely fine droplets of spray containing the nitroglycerin.

It is also an object of the invention to administer to a mammal in need of same preferably man, a predetermined amount of nitroglycerin by this method.

A further object is a sealed aerosol spray container containing a composition of the spray formulation, and a metered valve suitable for releasing from said container a predetermined amount of said composition.

As the propellant evaporates after activation of the aerosol valve, a mist of fine droplets is formed which contains solvent and nitroglycerin.

The propellant is a non-Freon material, preferably a $C_{3-8}$ hydrocarbon of a linear or branched configuration. The propellant should be substantially non-aqueous. The propellant produces a pressure in the aerosol container such that under expected normal usage it will produce sufficient pressure to expel the solvent from the container when the valve is activated but not excessive pressure such as to damage the container or valve seals.

The solvent is a non-polar hydrocarbon, preferably a $C_{7-18}$ hydrocarbon of a linear or branched configuration, its alcohols, and esters thereof, as well as triglycerides, such as miglyol. The solvent must dissolve the nitroglycerin and be miscible with the propellant, i.e., solvent and propellant must form a single phase at 0°–40° C. at a pressure range of 1–3 atm.

The spray compositions of the invention are intended to be administered from a sealed, pressurized container. Unlike a pump spray, which allows the entry of air into the container after every activation, the aerosol container of the invention is sealed at the time of manufacture. The contents of the container are released by activation of a metered valve, will does not allow entry of atmospheric gasses with each activation. Such containers are commercially available.

BRIEF DESCRIPTION OF THE DRAWING

The FIGURE is a schematic diagram showing routes of absorption and processing of pharmacologically active substances in a mammalian system.

DESCRIPTION OF THE PREFERRED EMBODIMENTS

Nitroglycerin is soluble in the non-polar solvents of the invention at useful concentrations. These concentrations may be less than the standard accepted dose for this compounds since there is enhanced absorption of the compounds through the oral mucosa. This aspect of the invention is especially important because there is a large (40–99.99%) First pass effect.

As propellants for the sprays, propane, N-butane, iso-butane, N-pentane, iso-pentane, and neo-pentane, and mixtures thereof may be used. N-butane and iso-butane, as single gases, are the preferred propellants. It is permissible for the propellant to have a water content of no more than 0.2%, typically 0.1–0.2%. (All percentages herein are by weight unless otherwise indicated.) It is also preferable that the propellant be synthetically produced to minimize the presence of contaminants which are harmful to the nitroglycerin. These con-taminants include oxidizing agents, reducing agents, Lewis acids or bases, and water. The concentration of each of these should be less than 0.1 %, except that water may be as high as 0.2%.

The solvent may be a selected from the group consisting of $C_{7-18}$ hydrocarbons of a linear or branched configuration, the alcohols thereof, the $C_{2-6}$ alkanoyl esters and triglycerides of $C_{7-18}$ carboxylic acids of a linear or branched configuration.

The preferred flavoring agents are synthetic or natural oil of peppermint, oil of spearmint, citrus oil, fruit flavors, sweeteners (sugars, aspartame, saccharin, etc.), and combinations thereof.

While certain formulations are set forth herein, the actual amounts to be admistered to the mammal or man in need of same are to be determined by the treating physician.

The invention is further defined by reference to the following examples, which are intended to be illustrative and not limiting.

EXAMPLE 1

Nitroglycerin Spray

A spray of the invention comprises the following formulation:

|  | Amount | Preferred Amount | Most-Preferred Amount |
|---|---|---|---|
| Propellant | 50–95% | 55–85% | 65–80% |
| Non-polar solvent | 5–50% | 15–45% | 20–35% |
| Nitroglycerin | 0.12–10% | 0.25–6.25% | 0.25–5% |
| Flavoring agent | 0.05–3% | 0.1–2.5% | 1–2% |

EXAMPLE 2

Nitroglycerin Spray

It is particularly preferred to formulate the spray delivering 0.4 mg of nitroglycerine/activation:

|  | Amount |
|---|---|
| n-butane | 67% |
| Miglyol | 30.75% |
| Nitroglycerin | 1.25% |
| Oil of Peppermint | 1.0% |

EXAMPLE 3

Nitroglycerin Spray

It is particularly preferred to formulate the spray delivering 0.4 mg of nitroglycerin/activation:

|  | Amount |
|---|---|
| iso-butane | 67.0% |
| miglyol | 30.75 |
| Nitroglycerin | 1.25% |
| Oil of Peppermint | 1.0% |

EXAMPLE 4

Nitroglycerin Spray

It is particularly preferred to formulate the spray delivering 0.1 mg of nitroglycerin/activation:

|  | Amount |
|---|---|
| n-butane | 33.75% |
| iso-butane | 33.75% |
| miglyol | 31.19% |
| Nitroglycerin | 0.31% |
| Oil of Peppermint | 1.00% |

What is claimed is:

1. A buccal aerosol spray composition for transmucosal administration of a pharmacologically nitroglycerin soluble in a pharmacologically acceptable non-polar solvent comprising in weight % of total composition: pharmaceutically acceptable propellant selected from the group consisting of $C_{3-8}$ hydrocarbon of a linear or branched configuration 50–95%, non-polar solvent 5–50%, and nitroglycerin 0.1–6.5%.

2. The composition of claim 1 additionally comprising, by weight of total composition: flavoring agent 0.05–5%.

3. The composition of claim 1 comprising: propellant 55–85%, non-polar solvent 15–45%, nitroglycerin 0.2–3.0%, flavoring agent 0.1–2.5%.

4. The composition of claim 1 comprising: propellant 60–80%, non-polar solvent 19–32%, nitroglycerin 0.3–1.5%, flavoring agent 1–2%.

5. The composition of claim 1 wherein the propellant is a $C_{3-8}$ hydrocarbon of a linear or branched configuration.

6. The composition of claim 1 wherein the propellant is propane, N-butane, iso-butane, N-pentane, iso-pentane, or neo-pentane, and mixtures thereof.

7. The composition of claim 1 wherein the propellant is N-butane or iso-butane and has a water content of no more than 0.2% and oxidizing agents, reducing agents, and Lewis acids or bases content in a concentration of less than 0.1%.

8. The composition of claim 1 wherein the solvent is a selected from the group consisting of $C_{7-18}$ hydrocarbons of a linear or branched configuration, and the $C_{2-6}$ alkanoyl esters and triglycerides of $C_{7-18}$ carboxylic acids of a linear or branched configuration.

9. The composition of claim 8 wherein the solvent consists of miglyol.

10. The composition of claim 2 wherein the flavoring agents are selected from the group consisting of synthetic or natural oil of peppermint, oil of spearmint, citrus oil, fruit flavors, sweeteners and combinations thereof.

11. The composition of claim 1 of the formulation: n-butane 67%, miglyol 30.75%, nitroglycerin 1.25%, flavoring agent 1.0%.

12. The composition of claim 1 of the formulation: isobutane 67%, miglyol 30.75%, nitroglycerin 1.25%, flavoring agent 1.0%.

13. The composition of claim 1 of the formulation: isobutane 33.75%, n-butane 33.75%, miglyol 31.19%, nitroglycerin 0.31%, flavoring agent 1.0%.

14. A method of administering a pharmacologically nitroglycerin to a mammal in needed of same, by spraying the oral mucosa of said mammal with a composition of claim 1.

15. The method of claim 14 wherein the amount of spray administered is predetermined.

16. A sealed aerosol spray container containing a composition of claim 1 and a metered valve suitable for releasing from said container a predetermined amount of said composition.

* * * * *

UNITED STATES PATENT AND TRADEMARK OFFICE
CERTIFICATE OF CORRECTION

PATENT NO.    : 5,869,082
DATED         : February 9, 1999
INVENTOR(S)   : Harry A. Dugger, III It is certified that error appears in the above-identified patent and that said Letters Patent is hereby corrected as shown below:

Column 4,
Line 1, insert -- non-Freon -- before "propellant".

Signed and Sealed this

Fifteenth Day of October, 2002

*Attest:*

*Attesting Officer*

JAMES E. ROGAN
*Director of the United States Patent and Trademark Office*